(12) United States Patent
Rath et al.

(10) Patent No.: US 7,861,591 B2
(45) Date of Patent: Jan. 4, 2011

(54) DEVICE FOR THE ULTRASONIC INSPECTION OF THE WELD SEAM OF LONGITUDINALLY WELDED PIPES FOR DEFECTS

(75) Inventors: Hans-Joachim Rath, Hamm (DE); Rainer Lücke, Münster (DE); Alfred Graff, Essen (DE)

(73) Assignee: Mannesmann Fuchs Rohr GmbH, Siegen (DE)

( * ) Notice: Subject to any disclaimer, the term of this patent is extended or adjusted under 35 U.S.C. 154(b) by 905 days.

(21) Appl. No.: 11/661,517

(22) PCT Filed: Apr. 5, 2005

(86) PCT No.: PCT/DE2005/000645

§ 371 (c)(1),
(2), (4) Date: Feb. 26, 2007

(87) PCT Pub. No.: WO2006/021167

PCT Pub. Date: Mar. 2, 2006

(65) Prior Publication Data

US 2009/0000379 A1    Jan. 1, 2009

(30) Foreign Application Priority Data

Aug. 27, 2004    (DE) ............... 10 2004 042 303

(51) Int. Cl.
*G01H 3/00*    (2006.01)
(52) U.S. Cl. ................... 73/592; 73/577; 73/597; 73/622

(58) Field of Classification Search ............ 73/584, 73/592, 573, 577, 587, 598, 600, 618, 623, 73/37, 37.5, 37.8; 219/91.1
See application file for complete search history.

(56) References Cited

U.S. PATENT DOCUMENTS

| | | | |
|---|---|---|---|
| 3,575,044 A * | 4/1971 | Gibbs et al. | 73/612 |
| 3,868,847 A | 3/1975 | Gunkel et al. | |
| 3,895,685 A * | 7/1975 | Gillette et al. | 181/5 |
| 3,921,440 A * | 11/1975 | Toth | 73/622 |
| 4,195,530 A * | 4/1980 | Ross et al. | 73/638 |

(Continued)

FOREIGN PATENT DOCUMENTS

DE    2854374 A1    6/1980

*Primary Examiner*—Hezron Williams
*Assistant Examiner*—Samir M Shah
(74) *Attorney, Agent, or Firm*—Duane Morris LLP; Lewis F. Gould, Jr.; Frank J. Spanitz

(57) ABSTRACT

The present invention pertains to a device for ultrasonic inspection of a weld seam of a longitudinally welded pipe for longitudinal defects with an inspection unit, which is relatively displaceable on a pipe surface on at least one side of the weld seam. The device also has two inspection heads in a tandem and spatially-variable arrangement, such that they can be positioned relative to the pipe surface to correspond to an intended acoustic irradiation angle independent of the diameter of the pipe. According to the invention, one inspection head acts as a transmitter and the other inspection head acts as a receiver. The device also has a pick-up connected to each of the two inspection heads, a coupling means connection connected to each pick-up, and a replaceable connecting element connected each pick-up via the coupling means connection.

16 Claims, 7 Drawing Sheets

U.S. PATENT DOCUMENTS

| | | | |
|---|---|---|---|
| 4,312,230 A * | 1/1982 | Bricker et al. | 73/638 |
| 4,641,529 A * | 2/1987 | Lorenzi et al. | 73/601 |
| 5,519,741 A * | 5/1996 | Suzuki et al. | 376/249 |
| 5,583,292 A * | 12/1996 | Karbach et al. | 73/638 |
| 5,677,490 A | 10/1997 | Guther et al. | |
| 6,178,819 B1 * | 1/2001 | Smartt et al. | 73/622 |
| 6,891,183 B2 * | 5/2005 | Kitamura et al. | 250/559.29 |
| 6,925,882 B1 * | 8/2005 | Fleming et al. | 73/632 |
| 6,931,931 B2 * | 8/2005 | Graff et al. | 73/622 |
| 7,234,347 B2 * | 6/2007 | Harthorn et al. | 73/152.57 |
| 7,448,272 B2 * | 11/2008 | Aznar et al. | 73/634 |
| 2004/0020298 A1 | 2/2004 | Siverling | |
| 2004/0237653 A1 * | 12/2004 | Graff et al. | 73/588 |
| 2007/0068286 A1 * | 3/2007 | Piper | 73/866.5 |

* cited by examiner

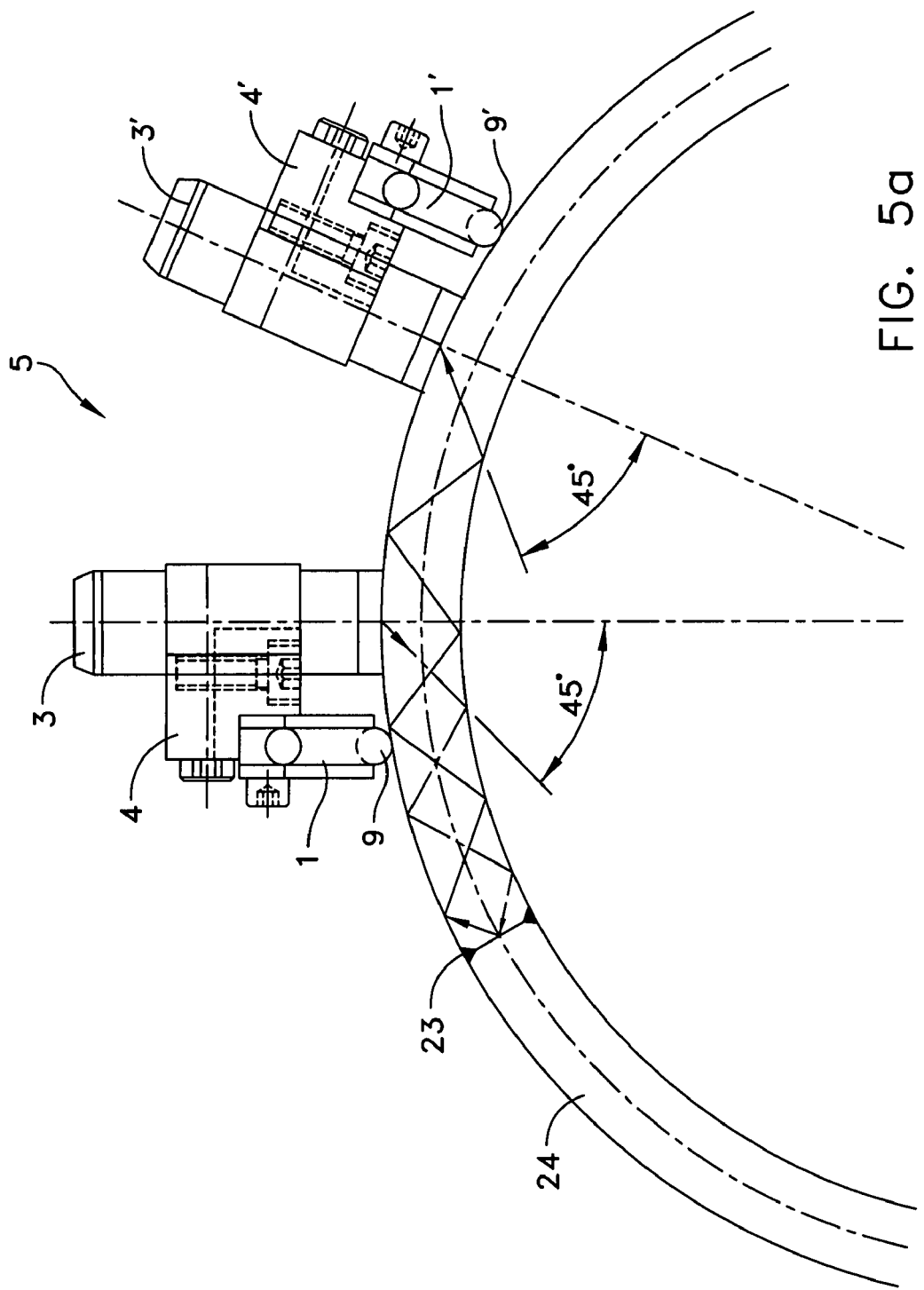

DEVICE FOR THE ULTRASONIC INSPECTION OF THE WELD SEAM OF LONGITUDINALLY WELDED PIPES FOR DEFECTS

BACKGROUND OF THE INVENTION

The present invention pertains to a device for the ultrasonic inspection of the weld seam of longitudinally welded pipes for longitudinal defects.

A device for the ultrasonic inspection of girth welds of pipes for longitudinal and transverse defects is published by Scott Lebsack and Helmut Heckhauser with the title "Immersion Probe Arrays for Rapid Pipeline Weld Inspection" in the journal Materials Evaluation (August 1995, pp. 886-891). This device has a holding system, in which two inspection head systems (arrays) are fastened. Each inspection head system has four inspection heads for inspection for longitudinal defects and one inspection head for inspection for transverse defects. The two inspection head systems for inspection for longitudinal defects are positioned on the right and left next to the girth weld, each inspection head acting as a transmitter and as a receiver at the same time, which detects a certain area of the seam in the direction of the depth.

The drawback of this prior-art device for inspecting girth welds is that it is not suitable for inspecting longitudinal welds of pipes for longitudinal defects, because no provisions are made for adapting the inspection head holder to the curvature of the pipe in case of arrangement in the circumferential direction of the pipe.

Moreover, it is not possible to reliably recognize all defects in the center of the weld due to the type of inspection with an inspection head acting as a transmitter and as a receiver at the same time. Longitudinal defects in the area of the center of the weld are detected by this technique only insufficiently if at all in case of greater wall thicknesses, e.g., >12.0 mm, precisely with the 45° inspection technique frequently specified in the inspection specifications, in which an acoustic irradiation angle of 45° relative to the pipe surface is specified.

DE 26 07 011 discloses a device for the ultrasonic inspection of the weld seam of submerged arc-welded large pipes, wherein at least four ultrasonic angle inspection heads are arranged on both sides of the weld seam and at different distances from the weld seam in an inspection area for inspection for longitudinal defects. One inspection head each on one side of the weld is located opposite another inspection head at equal distance from the weld on the other side of the weld. Each inspection head likewise acts as a transmitter and as a receiver of the ultrasound signal at the same time. The inspection area is determined by the series arrangement of the inspection heads along the weld seam, and the entire range of the weld thickness is to be covered by this series arrangement.

This device likewise has the above-described drawbacks of defect detection in the central area of the weld and additionally has the drawback that the device has a very complicated shape and adaptation to greatly different pipe diameters can be achieved in a highly complicated manner only.

Finally, reference shall be made to DE 101 34 696 C1, in which a device for the ultrasonic inspection of the weld seam of longitudinally welded pipes, among other things, for longitudinal defects, is likewise disclosed. This device also has an inspection head each, which acts as a transmitter and as a receiver at the same time, on each side of the weld, opposite each other, wherein flexible and rapid adaptation to different inspection tasks and pipe sizes is difficult due to the complicated shape of the device and the use of standard inspection heads.

BRIEF SUMMARY OF THE INVENTION

The object of the present invention is to propose a device for the ultrasonic inspection of the weld seam along longitudinally welded pipes for longitudinal defects, which makes possible better detection of defects in the central area of the weld as well. Another object shall be to make the design of the device simpler and thus to make possible a flexible and rapid adaptation to different inspection tasks and pipe sizes.

According to the teaching of the present invention, the inspection unit is equipped with two inspection heads, especially angle inspection heads in a tandem arrangement, the distance between which can be varied depending on the inspection task and the pipe geometry, wherein one angle inspection head acts as a transmitter and the other angle inspection head acts as a receiver, and the positions of the angle inspection heads in the inspection unit relative to the pipe surface can be adapted such that the inspection head can always be arranged in the position corresponding to the intended acoustic irradiation angle relative to the pipe surface independently from the pipe diameter. The mode of operation of an angle inspection head will be briefly described below for the better understanding of the solution according to the present invention.

The direction of sound propagation within the inspection head is preset in an angle inspection head, so that the acoustic irradiation into the pipe surface takes place in the direction (for example, 45°) preset within the inspection head in case of flat coupling of the inspection head on the pipe surface.

By contrast, standard inspection heads always perform acoustic irradiation at right angles into the pipe surface in case of flat coupling. If acoustic irradiation into the pipe surface is to be performed at a certain angle with standard inspection heads, the inspection head itself must be pivoted into the angular position corresponding to the intended acoustic irradiation angle.

Due to the inspection unit according to the present invention, the inspection heads are always arranged in such a position in the inspection unit that flat coupling with the pipe surface is now guaranteed in the desired position corresponding to the intended acoustic irradiation angle independently from the curvature or the diameter of the pipe.

Due to this tandem arrangement of the inspection heads in the device, longitudinal defects in the area of the center of the weld can be detected reliably and with sufficient sensitivity in a simple and effective manner even with the use of the 45° inspection technique.

The inspection unit proposed has, furthermore, the advantage that a maximum of reproducible settings is guaranteed at the same time in flexible adaptation to different inspection tasks and pipe geometries.

For flexible and rapid adaptation to different inspection tasks and pipe geometries, the inspection unit is advantageously of a modular design composed of standardized modular elements. These modules comprise:

a connecting element and two pick-ups, which can be connected thereto and accommodate the inspection heads, with a coupling means connection each, two longitudinal rails, which can be connected to the inspection unit, a connection coupling that can be connected to the inspection unit for the stationary positioning of the inspection unit in the inspection position on a stationary inspection frame, wherein the connecting element, presetting the angular position and the distance between the inspection heads, is sorted and put together in a preferred dimension grid for the angular position and the distance of the inspection heads replaceably and corresponding to the inspection task and the pipe geometry.

Adaptation of the inspection head position to different pipe diameters is accomplished in a simple manner by means of the variable angular position of the inspection heads in the connecting element, the inspection head being directed in relation to the pipe surface such that reproducible acoustic irradiation can take place at the preset acoustic irradiation angle of, e.g., 45°.

This adaptation to different pipe diameters is advantageously performed only by means of the replaceable connecting element, wherein a recess each, into which the two pick-ups for the inspection heads can be plugged and in which they can be fixed, is arranged on the inside at the longitudinal ends in a certain angular position.

The angular position of the recesses is adapted to the different pipe diameters such that the inspection heads perform acoustic irradiation into the pipe surface with the intended acoustic irradiation angle.

The adaptation to different inspection tasks and pipe geometries can be performed in a very simple and reproducible manner via the preset angular position of the recess and the length of the connecting elements, which determines the distance between the inspection heads. The pick-ups are preferably fixed to the connecting element by means of screws, which can be plugged into the pick-ups and screwed into the connecting element.

The pick-up itself is advantageously of a two-part design, comprising a base plate and a clamping element, which can be connected thereto. The base plate is provided with a circular recess, which surrounds the inspection head on a part of the circumference. For completely surrounding and clamping the inspection head in the base plate, the clamping element likewise has a complementary partial recess, in which case clamping is advantageously brought about by means of a screw connection between the clamping element and the base plate.

During the inspection proper, the longitudinally welded pipe with the longitudinal weld seam is passed through under the stationary inspection unit. To guarantee uniform contacting between the inspection heads and the pipe surface during the inspection, the inspection unit is guided on the pipe surface. The rail elements of the inspection unit are advantageously designed for this purpose as sliding skids, which slide on the pipe surface.

To minimize the wear resulting from the friction, the sliding skids are provided, on the contact surfaces with the pipe, with a wear protection, which may consist of a hard material, for example, hard metal or ceramic.

Another advantageous solution also consists of providing the longitudinal rails with low-wear rollers or with low-wear balls rotatable in all directions for rolling the inspection unit on the pipe surface.

To simplify the mounting of the inspection unit set up for the inspection on the stationary guide frame, the inspection unit is provided with a quick connection coupling. The connection coupling is connected pivotably at right angles to the longitudinal axis of the inspection unit to a bearing block, which is in turn connected to the connecting element in a positive-locking and non-positive manner to achieve reliable and rigid connection of the connection coupling to the inspection unit. The positive-locking connection is achieved here by means of a groove in the connecting element and a lug of the bearing block of the connection coupling, which lug meshes with the said groove. This connection is additionally secured by means of a screw connection in a non-positive manner.

The bearing block, rigidly connected to the inspection unit, has, at right angles to the longitudinal axis, a pivot axis, about which the connection coupling can pivot over a limited range. This pivotability facilitates the exact positioning of the inspection unit on the pipe surface. The presetting is then fixed in a simple manner by clamping the connection coupling with the bearing block by means of a clamping lever.

To simplify the positioning of the inspection unit on the pipe surface, the inspection unit is likewise connected to the connection coupling in such a way that it is rotatable about the longitudinal axis over a preset range of angles. The connection coupling is provided for this purpose with a connection sleeve, which can be rigidly connected to the stationary guide frame and in which a pin, which is rigidly connected to the bearing block, is arranged in such a way that it is rotatable over a preset range of angles and can be fixed in the particular position.

Further features, advantages and details of the present invention will appear from the following description of the exemplary embodiment shown.

BRIEF SUMMARY OF THE SEVERAL VIEWS OF THE DRAWINGS

FIG. 5a shows the arrangement of the inspection unit on a pipe with small diameter.

DETAILED DESCRIPTION OF THE INVENTION

Figure 1:
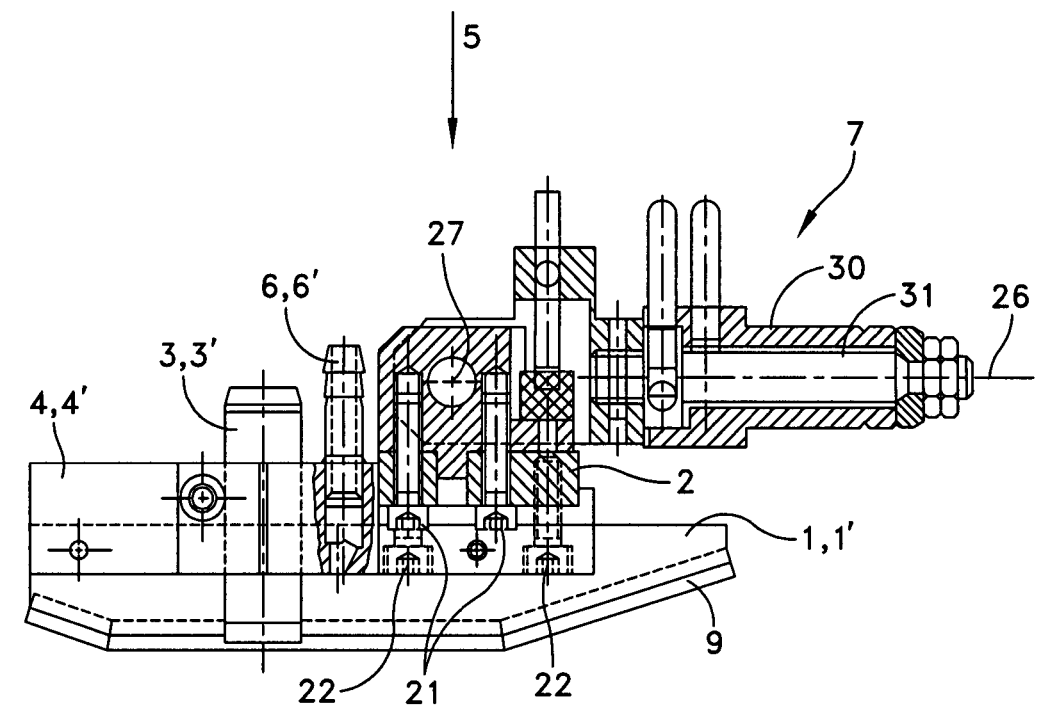
FIG. 1 shows a side view and a top view of an inspection unit designed according to the present invention for the inspection of longitudinal defects.
Figure 1:
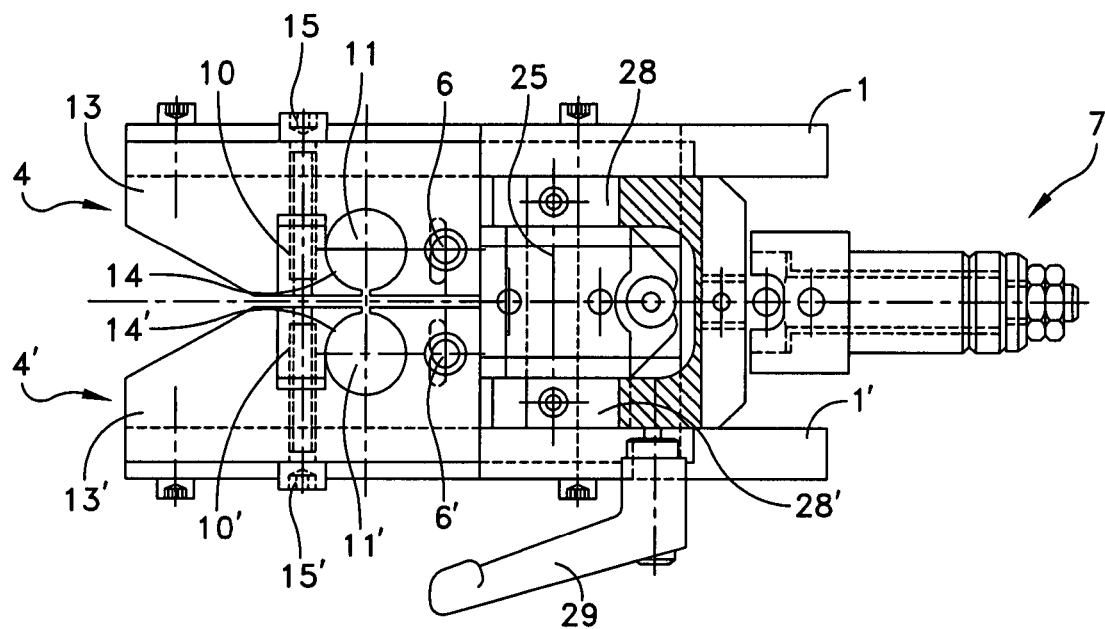

FIG. 1 shows a side view and a top view of an inspection unit 5 designed according to the present invention and composed of modules for the inspection of longitudinal defects on longitudinally welded pipes with two inspection heads 3, 3' designed as angle inspection heads. The inspection unit 5 comprises a standardized connecting element 2, which is interchangeable depending on the inspection task and which connects the pick-ups 4, 4' by means of the terminal recesses 8, 8' shown in FIG. 2a.

The adaptation of the inspection heads 3, 3' to different pipe geometries or inspection tasks is performed in a simple manner due to the oblique position of the recesses 8, 8' in the connecting element 2 as well as the distance between these recesses, so that the intended acoustic irradiation angle into the pipe and the detection of the echo signal can always be preset in a reproducible manner by the defined positioning of the inspection heads 3, 3' relative to the pipe surface.

The inspection heads 3, 3' are arranged in the inspection unit such that when the inspection unit is in the inspection position, the inspection heads are in contact with the pipe surface, as a result of which the acoustic irradiation angle relative to the pipe surface is fixed.

Figure 3:
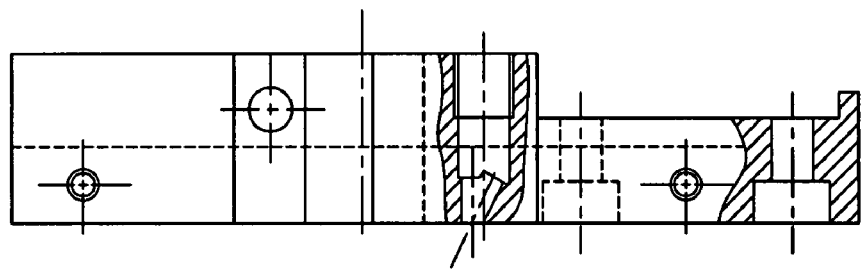
FIG. 3 shows a side view and a top view of a pick-up for an inspection head.
Figure 3:
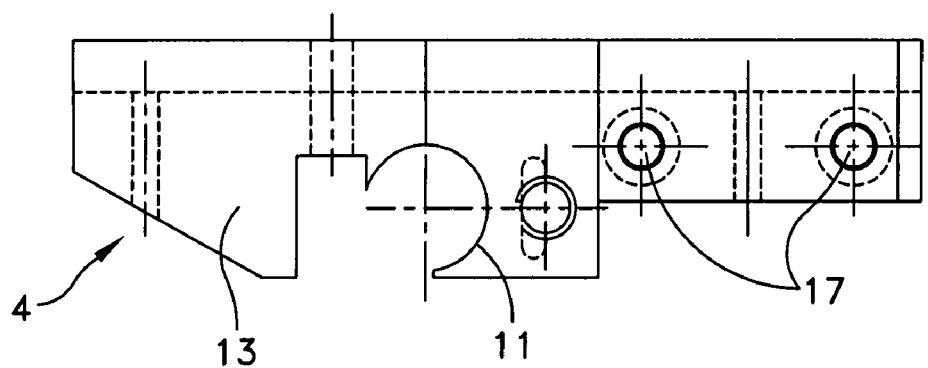
Figure 3:
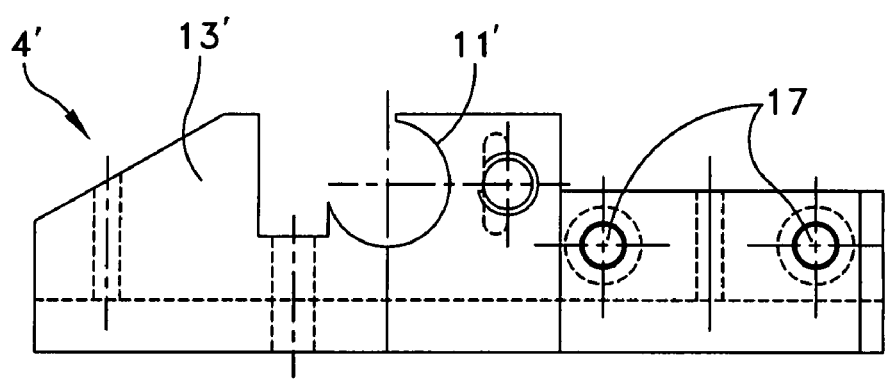

The pick-ups 4, 4' for the inspection heads 3, 3' are shown in detail in FIG. 3. The pick-ups 4, 4', arranged at the connecting element 2 on the right side and on the left side (see FIG. 1), comprise a base plate 13, 13', which are provided with a partial recess 11, 11' for the positive-locking mounting of the inspection heads 3, 3' shown in FIG. 1.

Figure 2A:
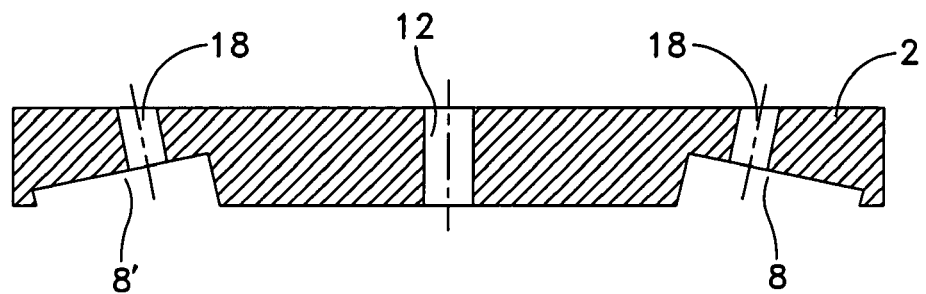
FIG. 2a shows a cross section and a top view of a connecting element for the inspection unit.
Figure 2A:
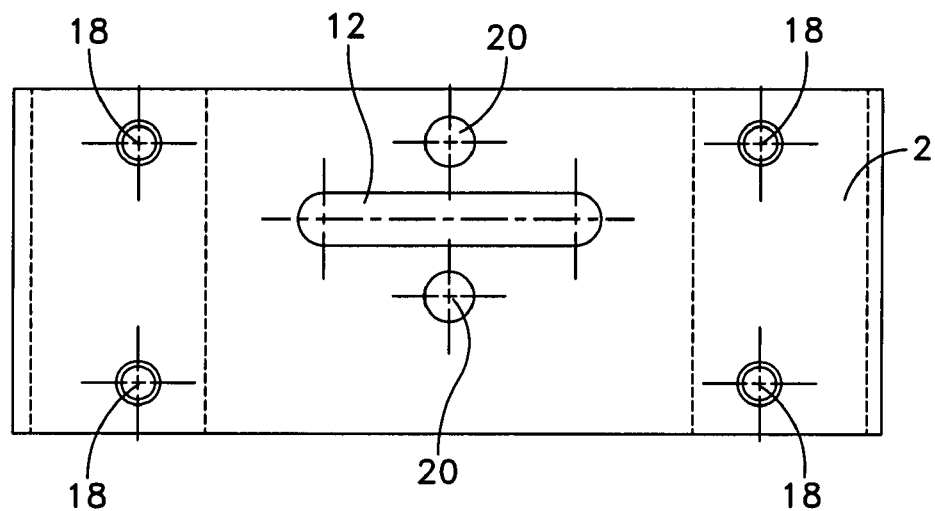

Via the holes 17 in the pick-up 4, 4', the pick-ups are connected to the connecting element 2 with a screw connection 22 via threaded holes 18 in a non-positive manner (cf. FIG. 2a).

As is apparent from FIG. 1, the inspection heads 3, 3' are positioned in a tandem positioning, one inspection head 3, 3' acting as a transmitter and the other inspection head 3, 3' as a receiver.

To fix the position of the inspection heads 3, 3' in the base plate 13, 13' of the pick-up 4, 4', a clamping element 10, 10', with which the inspection heads 3, 3' can be fixed in the base plate 13, 13' in a positive-locking and non-positive manner, is arranged at the base plate 13, 13'.

The clamping element 10, 10' is provided with another partial recess 14, 14' in order to surround the inspection head 3, 3' together with the base plate 13, 13' in a positive-locking manner. The non-positive clamping is achieved here by a screw connection 15, with which the inspection head 3, 3' is clamped in the partial recess 11, 11' of the base plate and the partial recess 14, 14' of the clamping element 10, 10'.

The fluid of the coupling means is supplied for the inspection heads 3, 3' via coupling means connections 6, 6' arranged at the respective pick-up 4, 4'.

Figure 4:
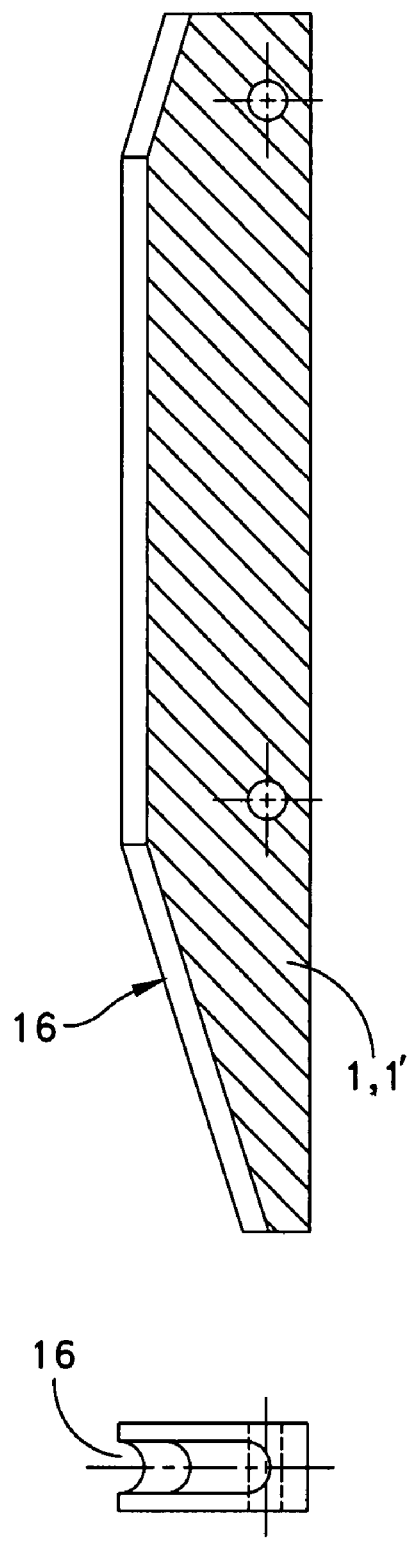
FIG. 4 shows a longitudinal view and a cross section of a longitudinal rail of the inspection unit.

To guide the inspection unit on the pipe surface, longitudinal rails 1, 1' are screwed on the outer sides of the pick-ups 4, 4'. The longitudinal rail 1, 1' is shown in more detail in FIG. 4. On the side touching the pipe surface, this rail 1, 1', designed as a sliding skid, has a groove 16, into which a hard metal bar, not shown here, can be inserted as a wear protection 9, for example, by soldering.

The inspection unit 5 is connected to a connection coupling 7 shown in FIG. 1 for stationary positioning on a stationary guide frame, which is likewise not shown here. For exact and reproducible fixation of the inspection position, the connection coupling 7, designed as a quick coupling, is mounted on a bearing block 25 in such a way that it can be pivoted in a limited range at right angles to the longitudinal axis 26 of the inspection unit 5.

The bearing block 25 itself is connected to the connecting element 2 of the inspection unit 5 in a positive-locking and non-positive manner. The connecting element 2 has a groove 12 for this, which meshes with a lug 19 arranged on the bearing block 25 in a positive-locking manner. The bearing block 25 is connected to the connecting element 2 in a non-positive manner by means of a screw connection 21 via holes 20.

To achieve pivotability, the bearing block 25 has, at right angles to the longitudinal axis 26 of the inspection unit 5, a pivot axis 27, on which the connection coupling 7 is mounted in such a way that it can be pivoted over a limited range and fixed in the particular position. The connection coupling 7 has a fork-shaped design for this purpose with legs 28, 28' at the bearing block-side end, the legs 28, 28' extending around the bearing block 25 and their ends forming a mounting point for the pivot axis 27. The particular pivoted position of the inspection unit 5 relative to the connection coupling 7 can be fixed in a simple manner by means of a clamping lever 29 due to clamping.

To simplify the positioning of the inspection unit on the pipe surface, the inspection unit 5 is connected, as is also shown in FIG. 1, to the connection coupling 7 rotatably about the longitudinal axis 26 over a preset range of angles. The connection coupling 7 is provided for this purpose with a connection sleeve 30, which can be rigidly connected to the stationary guide frame and in which a pin 31 connected to the bearing block 25 is arranged such that it can be rotated in a preset range of angles and fixed in the particular position. The fixation is brought about by means of another fixing lever, which is not shown here.

Figure 2B:
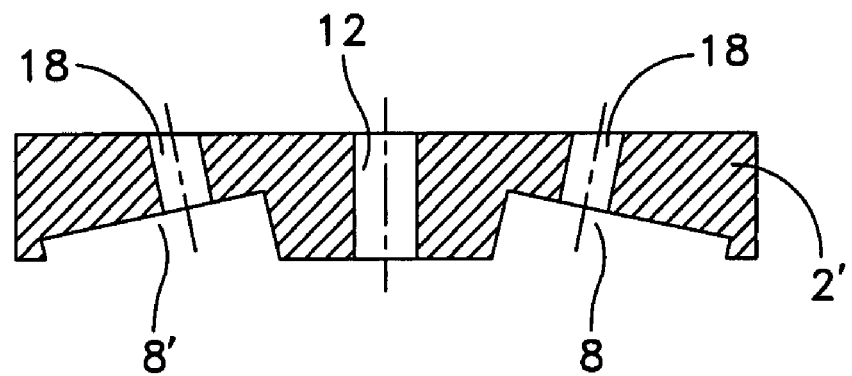
FIG. 2b is similar to FIG. 2a, but for another pipe geometry or inspection task.
Figure 2B:
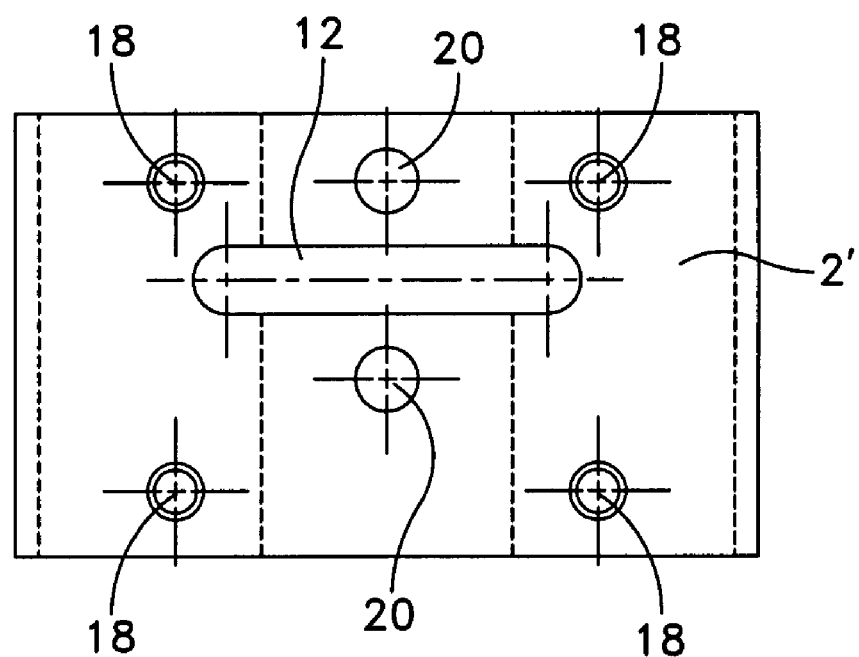

As is shown in FIG. 2b, only a correspondingly designed connecting element 2', which presets the angular position for the inspection heads 3, 3' by means of the slope of the recesses 8, 8' depending on the particular pipe diameter, is inserted into the inspection unit 5 for adaptation to different inspection tasks or pipe geometries, so that proper coupling with the pipe surface is guaranteed. Compared to the connecting element 2 in FIG. 2a, the slope of the recess 8, 8' determining the acoustic irradiation angle of the inspection head 3, 3' as well as the distance between the recesses 8, 8' are changed in the connecting element 2'.

FIG. 5a shows in a schematic diagram the tandem arrangement according to the present invention of the inspection heads 3, 3' on the pipe surface for one pipe dimension. For reasons of clarity, the inspection unit 5 is shown only with the essential elements, inspection heads 3, 3', pick-ups 4, 4' and longitudinal rails 1, 1' with the wear protection 9.

As is shown in this figure, the inspection is carried out from one side of the weld only. However, a further improvement of the reliability of the information obtained is achieved if the inspection is carried out with an inspection unit each from both sides of the weld.

The distance between the inspection heads 3, 3' as well as the angular position thereof in the inspection unit is set by means of the connection unit 2, which is not shown here. The inspection heads 3, 3' are positioned on the pipe surface such that the acoustic irradiation into the pipe surface takes place at the intended angle of 45°. Longitudinal defects that may be present in the central area of the weld are reliably detected with this acoustic irradiation angle.

The distance between the inspection heads 3, 3' is coordinated such that the irradiated signal detects the central area of the weld and the signal reflected by a flaw that may possibly be preset is received by the receiving inspection head 3, 3'. The signal course in the pipe wall is shown schematically.

The acoustic signal is emitted in this case by the inspection head 3, multiply reflected at the interface of the pipe wall (broken line), and the signal reflected by a defect in the weld seam 23 is received by the inspection head 3' (solid line). However, the functions of the inspection heads may also be transposed as needed.

In the prior-art devices for inspecting longitudinally welded pipes for longitudinal defects with an inspection head acting as a transmitter and as a receiver at the same time, a reflected signal (shown in an idealized form here) from the central area of the weld would not be able to be received at all or it would be able to be received at best as diffraction echoes, because the inspection head is located outside the range of detection for the reflected signal.

Figure 5B:
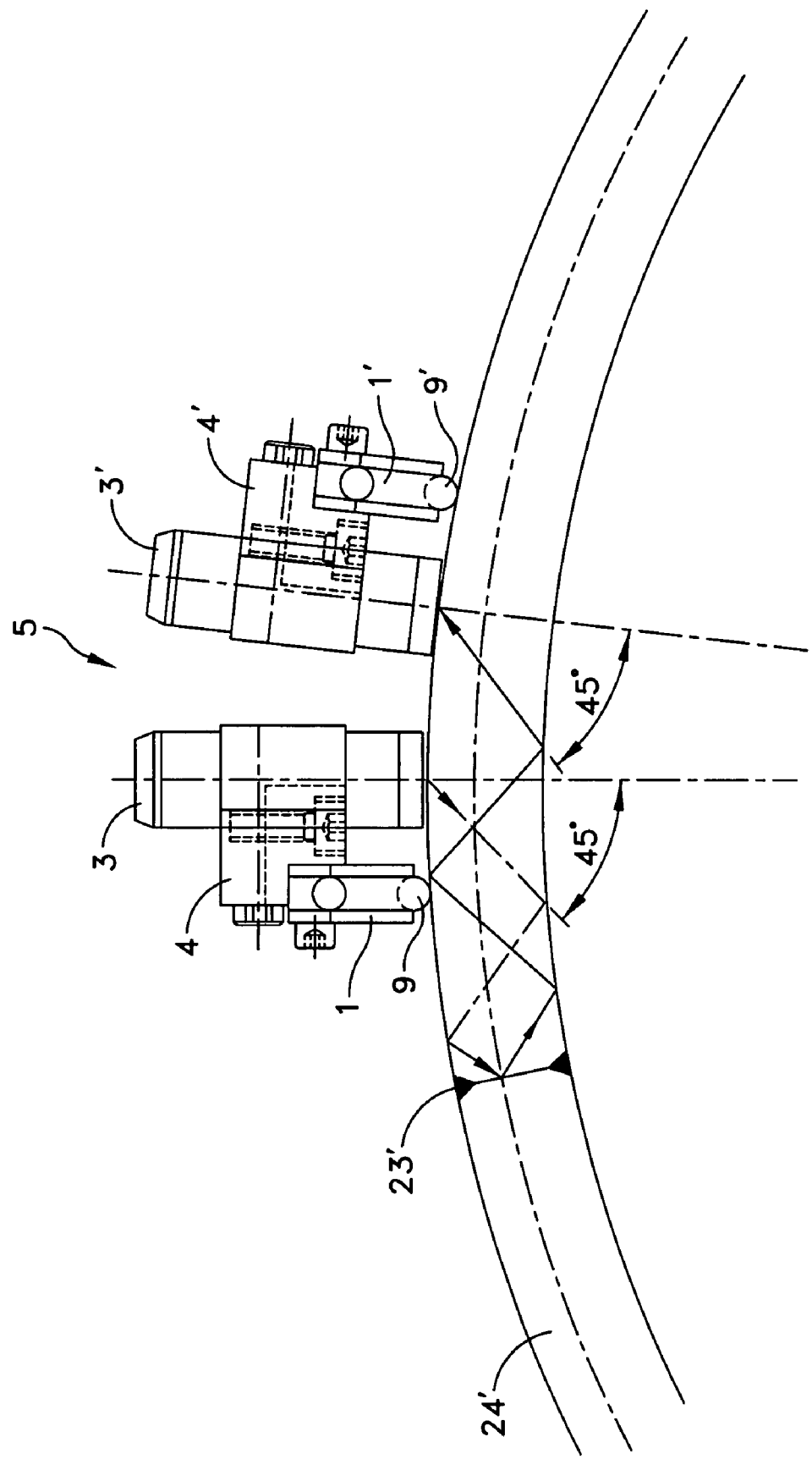
FIG. 5b is similar to FIG. 5a, but on a pipe with large diameter.

FIG. 5b shows an inspection unit 5, whose inspection heads 3, 3' are adapted to a larger pipe diameter for positioning corresponding to the intended acoustic irradiation angle.

The pipe 24' has a larger diameter as well as a greater wall thickness than the pipe 24 in FIG. 5a.

To detect the central area of the longitudinal weld 23' (at, e.g., 40% of the wall thickness here) during the ultrasonic inspection likewise at an acoustic irradiation angle of 45°, the inspection heads 3, 3' are arranged in a varied position for the angular position and distance within the inspection unit 5 compared to FIG. 5a, the position being likewise preset by means of the connecting element 2', which is likewise not shown here, and which is provided with a bent recess 8, 8' corresponding to the curvature of the pipe.

LIST OF REFERENCE NUMBERS

| No. | Name |
|---|---|
| 1, 1' | Longitudinal rail |
| 2, 2' | Connecting element |
| 3, 3' | Inspection head |
| 4, 4' | Pick-up |
| 5 | Inspection unit |
| 6, 6' | Coupling means connection |
| 7 | Connection coupling |
| 8, 8' | Recesses |
| 9 | Wear protection |
| 10, 10' | Clamping element |
| 11, 11' | Partial recess, base plate |
| 12 | Groove |
| 13, 13' | Base plate |
| 14, 14' | Partial recess, clamping element |
| 15 | Screw connection |
| 16 | Groove |
| 17 | Hole |
| 18 | Threaded hole |
| 19 | Lug |
| 20 | Hole |
| 21 | Screw connection |
| 22 | Screw connection |
| 23, 23' | Longitudinal weld seam |
| 24, 24' | Pipe |
| 25 | Bearing block |
| 26 | Longitudinal axis, inspection unit |
| 27 | Pivot axis |
| 28, 28' | Leg |
| 29 | Clamping lever |
| 30 | Connection sleeve |
| 31 | Pin |

The invention claimed is:

1. A device for ultrasonic inspection of a weld seam of a longitudinally welded pipe for defects comprising:
    an inspection unit, which is relatively displaceable on a pipe surface on at least one side of the weld seam,
    two inspection heads in a tandem arrangement, a distance between which inspection heads can be varied, that can be arranged relative to the pipe surface corresponding to an intended acoustic irradiation angle independent of the diameter of the pipe and further wherein one inspection head acts as a transmitter and the other inspection head acts as a receiver;
    a pick-up connected to each of the two inspection heads;
    a coupling means connection connected to each pick-up;
    a connecting element connected to each pick-up via the coupling means connection;
    longitudinal rails connected to the pick-ups and a connection coupling connected to the inspection unit on a stationary guide frame; and
    a bearing block connected pivotably to the connection coupling and connected in a positive-locking and non-positive manner to the connecting element.

2. The device of claim 1, wherein the connecting element has a recess accommodating each pickup.

3. The device of claim 2, wherein a slope of the recess determines the acoustic irradiation angle of the inspection head.

4. The device of claim 1, wherein the longitudinal rails are sliding skids.

5. The device of claim 4, wherein the sliding skids further comprise wear protection on a surface in contact with the pipe.

6. The device of claim 5, wherein the wear protection further comprises at least one hard metal.

7. The device of claim 5, wherein the wear protection further comprises at least one ceramic.

8. The device of claim 1, wherein the pick-up comprises a base plate having a partial recess for receiving an inspection head in a positive-locking manner and further comprising a clamping element connected to the base plate and having a partial recess for receiving the inspection head in a positive-locking manner.

9. The device of claim 8, wherein the clamping element is screwed to the base plate.

10. The device of claim 1, wherein the pick-ups are screwed to the longitudinal rails.

11. The device of claim 1, wherein the connection coupling is a quick coupling.

12. The device of claim 1, wherein the connecting element further comprises a groove and the bearing block further comprises a lug, the groove and lug through which the positive-locking connection between the connecting element and the bearing block is achieved.

13. The device of claim 1, wherein the bearing block is screwed to the connecting element.

14. The device of claim 1, wherein the bearing block further comprises a pivot axis at right angles to the longitudinal axis of the inspection unit.

15. The device of claim 1, wherein the connection coupling further comprises legs at the bearing block-side end that extend around the bearing block and form a mounting point for the pivot axis.

16. The device of claim 1, wherein the connection coupling further comprises a connection sleeve which can be rigidly connected to the stationary guide frame and a pin rigidly connected to the bearing block and further arranged so that the pin can be rotated over a preset range of angles and fixed in a particular position.

* * * * *